(12) United States Patent
Ferrand et al.

(10) Patent No.: US 9,388,468 B2
(45) Date of Patent: Jul. 12, 2016

(54) TRUNCATED CD20 PROTEIN, DELTACD20

(71) Applicant: ETABLISSEMENT FRANCAIS DU SANG (EFS), La Plaine Saint Denis (FR)

(72) Inventors: Christophe Ferrand, Dampierre (FR); Marina Deschamps, Besancon (FR); Carole Henry, Besancon (FR); Pierre Tiberghien, Paris (FR); Christophe Borg, Pouilley les Vignes (FR); Pierre-Simon Rohrlich, Besancon (FR)

(73) Assignee: ETABLISSEMENT FRANCAIS DU SANG, La Plaine Saint Denis (FR)

( * ) Notice: Subject to any disclaimer, the term of this patent is extended or adjusted under 35 U.S.C. 154(b) by 91 days.

(21) Appl. No.: 14/303,999

(22) Filed: Jun. 13, 2014

(65) Prior Publication Data
US 2014/0316125 A1 Oct. 23, 2014

Related U.S. Application Data

(62) Division of application No. 13/129,509, filed as application No. PCT/FR2009/001315 on Nov. 17, 2009, now Pat. No. 8,759,503.

(30) Foreign Application Priority Data

Nov. 18, 2008 (FR) ..................... 08 06444

(51) Int. Cl.
- C07H 21/04 (2006.01)
- C12P 21/06 (2006.01)
- C12Q 1/68 (2006.01)
- C07K 14/705 (2006.01)
- G01N 33/574 (2006.01)
- A61K 38/00 (2006.01)
- A61K 39/00 (2006.01)

(52) U.S. Cl.
CPC ........ *C12Q 1/6881* (2013.01); *C07K 14/70596* (2013.01); *G01N 33/57426* (2013.01); *A61K 38/00* (2013.01); *A61K 2039/57* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

2004/0219224 A1 11/2004 Yakovlevsky et al.

OTHER PUBLICATIONS

International Search Report of PCT/FR2009/001315; Mar. 4, 2010; Gurdjian, Didier.
Stamenkovic et al.: "Analysis of Two cDNA Clones Encoding the B Lymphocyte Antigen CD20 (B1, Bp35), A Type III Integral Membrane Protein", The Journal of Experimental Medicine, Rockefeller University Press, vol. 167, No. 6, Jun. 1, 1988, pp. 1975-1980.
"*Homo sapiens* cDNA FLJ51650 Complete CDS, Moderately Similar to B-Lymphocyte Antigen CD20", Database EMBL, Jul. 24, 2008, Database Accession No. AK300025.
Deschamps et al.: "A New Human CD20 Spliced mRNA as a Potential Molecular Marker for the Follow-up of B-Cell Malignancies", Database Biosis, Biosciences Information Service, Nov. 2008, Database Accession No. PREV200900258179.
50th Annual Meeting of the American Society of Hemalogy, Blood, vol. 112, No. 11, Nov. 16, 2008, p. 526.
Einfeld et al.: "Molecular Cloning of the Human B cell CD20 Receptor Predicts a Hydrophobic Protein with Multiple Transmembrane Domains", EMBO Journal, vol. 7, No. 3, Jan. 1, 1988, pp. 711-717.
Cragg et al.: "The Biology of CD20 and its Potential as a Target for mAb Therapy", Current Directions in Autoimmunity, Jan. 1, 2005, pp. 140-174.
Liang et al.: "Structural Organization of the Human MS4A Gene Cluster on Chromosome 11q12", Immunogenetics, vol. 53, No. 5, Jul. 1, 2001, pp. 357-368.

*Primary Examiner* — Catherine S Hibbert
(74) *Attorney, Agent, or Firm* — BCF LLP

(57) ABSTRACT

Diagnostic kit comprising an oligonucleotide probe for the mRNA encoding a polypeptide having an amino acid sequence substantially identical to that of SEQ ID NO: 2.

2 Claims, No Drawings

TRUNCATED CD20 PROTEIN, DELTACD20

CROSS-REFERENCE

The present application is a divisional of U.S. patent application Ser. No. 13/129,509, filed Aug. 30, 2011, which is a national phase entry of International Patent Application No. PCT/FR2009/001315, filed Nov. 17, 2009, which claims priority to French Patent Application No. 0806444, filed Nov. 18, 2008, the entirety of all of which is incorporated herein by reference.

The present invention relates in particular to a protein from an alternative splicing of the gene encoding CD20, the nucleic acid encoding the protein according to the invention, a mutated form of the CD20 gene as well as drugs, diagnostic tools, diagnostic methods and treatment methods using the protein and the nucleic acid sequences according to the invention.

The CD20 protein expressed on B lymphocytes is encoded by a gene belonging to a family located on chromosome 11 in the q12 region. This region defines a gene cluster named MS4A (Membrane Spanning 4 domain Subfamily A), with 12 subgroups referred to as MS4A1 to MS4A12. This gene cluster covers 600 Kb. The entire CD20 gene covers 41.17 Kb divided between 8 exons separated by 7 introns.

The CD20 pre-messenger RNA has a size of 14.95 KB with an untranslated 5' sequence (5'UTR) having 416 bp. The 3'UTR region has 2291 bp followed by a polyA extension and would appear to correspond to a regulation sequence. The sequence potentially encodes a protein having 297 amino acids (AA) for a predictive molecular weight of 33.0 KDa. Various splicing sites have been identified in the 5'UTR region, more specifically in exon 1, generating three forms of transcripts of different sizes varying by 2.8, 2.6 and 3.4 kb.

The various transcript forms encode CD20 protein having a molecular weight of 33 KD; however, by Western blot and immunoprecipitation, the presence of 3 isoforms of 33, 34.5 and 36 KD has been demonstrated, not corresponding to the spliced variants but to post-transcription modifications, by phosphorylation. This protein consists of a very hydrophobic region, 4 transmembrane segments (AA 68 to 84), defining an extracellular domain (AA encoded by exon VI) and an intracellular domain (AA encoded by exon III, V, VII and VIII).

Although widely used as a peripheral blood B lymphocyte marker, in lymphocyte population characterisation techniques or in the diagnostics of diseases or B haemopathies, the function of the CD20 protein has not been elucidated to date. However, the protein structure of the human or mouse CD20 molecule is similar to other proteins such as rhodopsin, Gap junction proteins or some adrenergic receptors, all involved in signal transduction, implying a similar role of the protein. The intracellular portion of this protein comprises numerous phosphorylation sequences and is associated with src family tyrosine kinases (Fyn, Lyn, Lck).

In vitro and Knock-Out (KO) mouse model functional studies for CD20 have shown that this protein was involved in inter-membrane Ca++ transport. The bond of an anti-CD20 Ab with this molecule also induces an increase in c-Myc and B-Myb oncogenes, an increase in intracellular protein phosphorylation, an increase in CD18, CD58 and class II MHC molecules along with tyrosine kinase activation inducing B cell adhesion. These functions attributed to CD20 protein remain controversial, since the development and function of B cells in a KO mouse model for CD20 have not been reported as normal and do not exhibit particular phenotype abnormalities.

A further function has been attributed to CD20 protein, that of cell cycle regulation in B lymphocyte (BL) differentiation and the activation/maturation thereof to plasmocytes. In B lymphocyte ontogenesis, CD20 is expressed in large quantities on the surface of pre-B cells (absent on pro-B), after the rearrangement of the genes encoding heavy Ig chains, with persistent membrane expression to the mature terminal B stage. CD20 is not expressed on haematopoietic stem cells, on pro-B cells, and plasmocytes, except for a small contingent of cells, in some pathological circumstances, which could correspond to plasmoblasts. Finally, note that the CD20 ligand is not known, rendering the determination of the function thereof difficult.

Expression on the surface of B lymphocytes enables the characterisation of this population in flow cytometry or use in immuno-magnetic purification techniques. Expression of the CD20 molecule on the majority of B cells, involved in malignant diseases makes it a therapeutic target of choice for a number of reasons:
- Marker present on BLs and absent on stem cells and plasmocytes
- It is expressed in large quantities on the cell surface
- It is not secreted or released into the circulation after proteolysis
- After anti-CD20 fixation, the CD20/Ab complex is not internalised Rituximab (Rx, trade name: Mabthera™) is a humanised mouse chimeric antibody against CD20 antigen. It is active against the malignant cells presenting CD20 antigen, i.e. in stage III-IV follicular lymphoma and in aggressive diffuse large B cell non-Hodgkin's lymphomas, positive for CD20. It is also used, optionally associated with chemotherapy, and more experimentally in other conditions, such as for example some autoimmune diseases, such as lupus or rheumatoid arthritis.

The Fc portion of human IgH has been selected for the ability thereof to fix the complement and induce ADCC (Antibody-Dependent Cell-Mediated) cytotoxicity. The factors influencing the efficacy thereof are diverse: CD20 surface expression density, antibody diffusion, therapeutic anti-CD20 antibody capture, antibody/target bonding, FcgR3 receptor polymorphism.

The present invention is based on the discovery of alternative splicing of the gene encoding CD20 giving rise to the expression of a truncated form of CD20. This polypeptide (i.e. deltaCD20 or ΔCD20) is deleted of all or part of the transmembrane part of the native CD20 (or wtCD20), which does not allow the deltaCD20 to be fixed on the B lymphocyte membrane.

In this way, in a first embodiment, the present invention relates to a polypeptide characterised in that it comprises an amino acid sequence substantially identical to that of SEQ ID NO: 2.

Within the scope of the present invention, the term "substantially identical" refers to two sequences having more than 90%, preferably 95%, more preferably 99% and most preferably 100% homology.

Within the scope of the present invention, the term "polypeptide" refers to an amino acid optionally comprising post-translation modifications. Preferably, the polypeptide according to the invention is obtained by means of synthesis or genetic engineering; in the latter case, the term recombinant protein is used.

Preferably, the polypeptide according to the invention has an amino acid sequence substantially identical to that of SEQ ID NO: 2 and more preferably, it is a polypeptide having the sequence SEQ ID NO: 2.

For clarity purposes, it is specified that the polypeptide according to the invention is particularly differentiated from wtCD20 (the amino acid sequence of which is represented by SEQ ID NO: 4) in that it cannot be associated with the cell membrane. In this way, it is also possible to characterise the polypeptide according to the invention in that it does not comprise a sequence of at least twenty consecutive amino acids from the sequences of twenty consecutive amino acids found between the amino acid in position 43 and the amino acid in position 209 of SEQ ID NO: 4 (i.e. the transmembrane part of wtCD20).

The present invention also relates to a nucleic acid sequence characterised in that it encodes a polypeptide according to the invention. According to one preferred embodiment, the nucleic acid sequence according to the invention comprises a nucleic acid sequence identical to SEQ ID NO: 1. According to a more preferable embodiment, the nucleic acid sequence according to the invention is identical to SEQ ID NO: 1.

Within the scope of the present invention, the term "nucleic acid sequence" particularly refers to natural or synthetic DNA or RNA sequences. Preferably, the nucleic acid sequence according to the invention is synthetic or obtained by means of genetic engineering. According to a further preferred embodiment, it consists of a completely or partially purified nucleic acid sequence.

The present invention also relates to a recombinant vector comprising a nucleic acid sequence according to the invention placed under the control of one or a plurality of elements required for the expression thereof in a host cell. Recombinant vectors are well known to those skilled in the art, they particularly enable the production of recombinant proteins and/or the multiplication of a nucleic acid sequence. Numerous recombinant vectors are available in the prior art, plasmids and viral vectors can particularly be cited. In this way, according to one preferred embodiment, the recombinant vector according to the invention is selected in the group comprising plasmids and viral vectors.

According to a first embodiment, the recombinant vector according to the invention is a viral vector. Viral vectors are well known to those skilled in the art and are already used in clinical practice in humans (e.g. MVA, adenovirus, retrovirus). They generally consist of a vector comprising all or part of the genome of a virus modified to incorporate an exogenous sequence. According to a preferred embodiment, the viral vector according to the invention is selected in the group comprising adenovirus vectors, retrovirus vectors, poxvirus vectors, herpes virus-derived vectors, vectors derived from viruses associated with adenoviruses and alphavirus-derived vectors. The present invention also relates to viral particles comprising the recombinant vectors according to the invention.

Preferably, the recombinant vector according to the invention is associated with one or a plurality of compounds facilitating the introduction thereof into a host cell. The compounds facilitating the introduction of a vector into a host cell are well known to those skilled in the art and some are commercially available, the term transfection agent is also used. In one particularly preferred embodiment, the compound facilitating the introduction of a recombinant vector according to the invention into a host cell is selected in the group comprising cationic lipids, calcium salts, cationic polymers and polypeptides.

Within the scope of the present application, the term "element required for expression in a host cell" refers to nucleic acid sequences for the translation and transduction of a nucleic acid sequence and nucleic acid sequences for increasing said transductions and translation. According to one preferred embodiment, the element required for expression in a host cell is selected in the group comprising introns, polyadenylation sites and promoters.

Within the scope of the present invention, the term host cell particularly refers to prokaroyote and eukaryote cells. Of these cells, bacteria, yeasts, insect cells (e.g. sf9) and animal cells (e.g. CHO, 293, PERC6) can be cited. The present invention also relates to a host cell comprising a recombinant vector according to the invention.

The applicants also revealed that the expression of deltaCD20 was correlated with the presence of some diseases. Furthermore, it was also revealed that the expression level of deltaCD20 is correlated with the progression of these diseases. This applies more specifically to diseases associated with B lymphocyte dysfunction (also known as B haemopathies) representing 85 to 90% of lymphoid haemopathies. These particularly consist of Follicular Lymphomas (FL), Chronic lymphocytic leukaemia (CLL), B-cell acute lymphoblastic leukaemia (ALL), mantle cell lymphoma (ML), B-cell lymphomas, Myeloma, Waldenström's Disease (WD).

In this way, the present invention also relates to an in vitro diagnostic method using a biological sample from a patient characterised in that it comprises the measurement of the expression level of a polypeptide according to the invention and/or mRNA encoding a polypeptide according to the invention.

The term "biological sample" refers to any fluids or tissues containing the patient's B lymphocytes. Preferentially, the biological sample is the patient's blood or bone marrow.

The method according to the invention can be implemented with an unprocessed biological sample (i.e. as sampled without undergoing any modification), but also after treating the biological sample by any methods deemed to be required by those skilled in the art. These treatments include erythrocyte lysis, mononuclear cell isolation (e.g. isolation on Ficoll) and/or the addition of molecules for preserving the biological sample (e.g. antiproteases). Techniques such as erythrocyte lysis and mononuclear cell isolation particularly make it possible to increase the proportion of B lymphocytes in relation to the other cells present in the biological sample. In this way, according to one preferred embodiment, the diagnostic method according to the invention further comprises a step for increasing the proportion of B lymphocytes in relation to the other cells present in the biological sample.

The polypeptide may consist of the protein before or after post-translation modifications and whole or cleaved. The method relates to the detection of all or part of the polypeptide, and it is thus possible to only detect part of the mRNA or polypeptide, in that the expression level of this part is representative of the expression of the entire molecule.

In the present application, the term "expression level" refers to the quantity of deltaCD20 expressed by the cells. The expression level can be measured quantitatively or semi-quantitatively; indeed, it is not necessary to know the exact quantity of deltaCD20, expressed by the cells, but merely determine whether this quantity is significantly greater than a specification. This can be readily determined by those skilled in the art using a pool of healthy subjects and measuring the expression level of deltaCD20 in the cells of these subjects. If the method according to the invention reveals a deltaCD20 expression level in patients' cells greater than the normal expression, said patient would be liable to suffer from B lymphocyte dysfunction.

According to a preferred embodiment, the measurement of the expression level of the polypeptide according to the invention is the measurement of the expression level of the mRNA encoding said polypeptide. Techniques for measuring the quantity of mRNA specifically encoding a molecule are well known to those skilled in the art. These techniques include quantitative RT-PCR, semi-quantitative RT-PCR, Northern Blot and the microarray technique. The design and production of the probes and oligonucleotides required to implement these techniques are within the scope of those skilled in the art. These oligonucleotides particularly include those described by SEQ ID NO: 14 to SEQ ID NO: 17 which are also the subject matter of the present invention. In this way, according to a more preferred embodiment, the expression level of the mRNA encoding the polypeptide according to the invention is measured by quantitative RT-PCR, semi-quantitative RT-PCR, real-time RT-PCR, Northern Blot or by the microarray technique.

According to a further preferred embodiment, said measurement of the expression level of a polypeptide according to the invention and/or mRNA encoding a polypeptide according to the invention is the measurement of the expression level of a polypeptide according to the invention and/or mRNA encoding a polypeptide according to the invention inside the B lymphocytes.

According to a preferred embodiment, said measurement of the expression level of a polypeptide according to the invention is carried out by an immunological method. Within the scope of the present application, the term "immunological method" refers to protein detection techniques making use of specific antibodies for said protein. Within the scope of the present application, the term "antibody" refers to a polypeptide comprising at least one paratope. The antibodies include T cell receptors, immunoglobulins, chimeric antibodies, human antibodies, monoclonal antibodies, humanised antibodies, recombinant antibodies and antibody fragments. The antibody fragments include Fab, Fab', F(ab)2, F(ab')2, Fv and scFv.

In this way, according to an even more preferred embodiment, the diagnostic method according to the invention further comprises a step wherein the polypeptide according to the invention is placed in contact with the specific antibody for said polypeptide.

The techniques for measuring the expression level of an intracellular protein are well known to those skilled in the art. They include, in particular, ELISA, flow cytometry, Western Blot. In this way, according to an even more preferred embodiment, the immunological method is selected from the group including ELISA, flow cytometry, Western Blot.

The immunological methods may be particularly used on cell lysates or on cells wherein the membrane is permeabilised to enable the passage of the antibodies inside the cell.

According to a preferred embodiment, the diagnostic method according to the invention is a method for diagnosing a disease associated with dysfunction of one or a plurality of the patient's B lymphocytes. According to a preferred embodiment, the disease associated with dysfunction of one or a plurality of B lymphocytes is selected in the group comprising Follicular Lymphomas (FL), Chronic lymphocytic leukaemia (CLL), B-cell acute lymphoblastic leukaemia (ALL), mantle cell lymphoma (ML), B-cell lymphomas, Myeloma, Waldenström's Disease (WD).

In solid organ transplantation, including kidney transplantation, allogenic graft loss remains a major problem. The role the donor's allo-antibody mechanisms in hyperacute rejection is well known and partially controlled, along with T-cell-related early and delayed rejection. However, treatments affecting the T lymphocyte compartment have a reduced impact on long-term graft survival, suggesting other target effector mechanisms.

The splicing of the identified CD20 gene generates deleted transcripts the sequence of which remains within the reading frame. Transcription of the spliced form of the mRNA or the translation into protein could interfere with expression of the normal CD20 protein and impair the surface expression thereof, which may modulate the efficacy of the Rituximab treatment. This was recently reported in the literature, where resistance acquisition to an anti-CD20 antibody (Rituximab) in lymphoma cell lines is associated with pre- and post-transcription regulation phenomena or epigenetic phenomena. In this way, deltaCD20 protein thus represents a novel therapeutic target for improving Rituximab treatment efficacy and prevent escape and relapse.

In kidney transplantation, a high-throughput transcriptome study, on patients suffering from acute rejection, made it possible to define a characteristic gene cluster of the B lymphocyte population, characteristic of some types of acute rejection, not conventionally distinguishable in optical microscopy. Supplementary studies with immunohistochemistry techniques have confirmed a strong presence of CD20+ B lymphocyte infiltrating the graft. Finally, the persistence of CD20+ cells infiltrating the kidney transplant post-treatment with Rituximab was demonstrated, whereas the circulating B Lymphocyte pool was removed.

Following this research, teams have described studies reporting anti-CD20 antibody (Rituximab) treatment for kidney or heart transplants with corticoids, ATG and plasmapheresis, the results were encouraging with 85% survival of the grafts at 2 years.

As a general rule, in solid organ transplantation, there is increasing interest in the B lymphocyte compartment, involved in allo-antibody production. Of the agents targeting this B lymphocyte populations, Rituximab naturally demonstrates the interest thereof in inhibiting the B response, both for preventive (pre-transplantation) and delayed treatment (targeting memory B cells). The use of the diagnostic method according to the invention (e.g. in biopsy fragments or on non-invasive urine samples) and our immunotherapy strategy targeting ΔCD20 protein are useful in predicting acute rejection and in improving Rituximab treatment.

In this way, according to a preferred embodiment, the disease associated with dysfunction of one or a plurality of B lymphocytes is acute transplant rejection.

In this way, according to a further preferred embodiment, the diagnostic method according to the invention is a method for assessing the efficacy of a treatment comprising the use of an anti-CD20 antibody. According to a preferred embodiment, said anti-CD20 antibody is Rituximab.

The present application also relates to a kit for implementing the diagnostic method according to the invention. In this way, the present invention also relates to a diagnostic kit comprising at least one specific antibody for the polypeptide according to the invention. The presence in deltaCD20 of at least one novel epitope in relation to the wild form of CD20 enables specific antibody production for deltaCD20. Those skilled in the art are fully capable of producing said antibodies by numerous methods available in the prior art. These particularly include screening of banks of phages expressing scFv. In this way, the present invention also relates to a specific antibody for the polypeptide according to the invention. According to a preferred embodiment, the antibody according to the invention is not specific for the wild form of CD20 and more specifically the polypeptide having a sequence as defined by SEQ ID NO: 4.

According to a further embodiment, the diagnostic kit according to the invention comprises at least one specific oligonucleotide probe for the mRNA encoding a polypeptide according to the invention. According to a preferred embodiment, said oligonucleotide probe comprises a sequence identical to SEQ ID NO: 14 or SEQ ID NO: 17. According to a particularly preferred embodiment, said oligonucleotide probe has a sequence identical to SEQ ID NO: 14 or SEQ ID NO: 17.

The present invention also relates to the use of a diagnostic kit according to the invention for detecting a disease associated with dysfunction of one or a plurality of B lymphocytes. According to a preferred embodiment, said disease associated with dysfunction of one or a plurality of B lymphocytes is selected in the group comprising Follicular Lymphomas (FL), Chronic lymphocytic leukaemia (CLL), B-cell acute lymphoblastic leukaemia (ALL), mantle cell lymphoma (ML), B-cell lymphomas, Myeloma and Waldenström's Disease (WD). According to a further preferred embodiment, said disease associated with dysfunction of one or a plurality of B lymphocytes is acute transplant rejection.

The present invention also relates to the use of a diagnostic kit according to the invention for evaluating the efficacy of a treatment comprising the use of an anti-CD20 antibody. According to a preferred embodiment, said anti-CD20 antibody is Rituximab.

The polypeptide according to the invention is an ideal target for an immunotherapy strategy (vaccination). More specifically, this immunotherapy strategy is useful for diseases associated with treatments using anti-CD20 antibodies (e.g. Rixtuximab) to prevent resistances and improve the treatment. Indeed, the inventors demonstrated using Western Blot an increase in the signal generated by the truncated protein in cases of Rituximab resistance, induced in vitro (B line with Rituximab selection pressure), correlated with the increase in the signal obtained with quantitative RT-PCR using mRNA from the same populations. This means that the cells expressing the most deltaCD20 escape and resist standard Rituximab treatment. The truncated protein, deltaCD20, is a potential protein target, for a T cytotoxic cellular response. Similarly, the spliced mRNA, also described, is a target of interest, using antisense oligonucleotide technologies or with silencing RNA approaches (SiRNA). The purpose of these two approaches is that of enabling the in vivo extinction of this alternative splicing. In this way, the present invention also relates to a method for improving a treatment, comprising the use of an anti-CD20 antibody, comprising the use of an anti-sense oligonucleotide and/or siRNA capable of completely or partially inhibiting the expression of a polypeptide according to the invention by the patient's cells.

Peptide vaccination or immnunotherapy is a therapeutic approach currently the subject of major interest in cancer prevention or treatment. The principle thereof is based on immunisation with peptides reproducing T epitopes of tumour antigens recognised by cytotoxic T lymphocytes (CTLs), playing a major role in the elimination of cancer cell expressing these antigens on the surface thereof.

CTLs do not recognise whole protein antigens, but peptide fragments thereof, presented by the major histocompatibility complex (MHC) molecules expressed on the surface of various cells. These peptide fragments form the T epitopes.

The presentation of these peptides is the result of a complex process, referred to as "antigen preparation" involving 3 main steps: 1/cytosolic antigen degradation by a multi-enzyme complex referred to as proteasome, 2/translocation of the peptides obtained from said degradation in the endoplasmic reticulum (ER) by TAP transporters, 3/association of these peptides with MHC to form stable peptide/MHC complexes, to be exported to the cell surface.

The epitopes presented by major histocompatibility complex class I (MHC I) generally have 8 to 11 amino acids, and are recognised by CD8+ T cells, representing the major component of the cytotoxic response.

The identification of these epitopes, in particular (in view of the essential role of the CD8+ response in cytotoxicity) those presented by MHC I, thus represents an essential step for anti-tumour immunotherapy development.

Numerous tumour antigens capable of inducing a CTL response are known at the present time. Some of the T epitopes of these antigens have been identified, and the efficacy of peptide-based vaccines reproducing these T epitopes has been demonstrated in numerous cases.

Following the discovery of a novel alternative splicing of the human CD20 gene (deltaCD20) and the discovery of a protein encoded by said truncated mRNA, the applicant discovered the impact of such a target in anti-tumour immunotherapy. Indeed, the results obtained demonstrate a role of this target protein (not expressed in healthy donors' B lymphocytes) in oncogenesis and the role thereof in anti-CD20 antibody (Rituximab) treatment resistance.

The discovery of deltaCD20 protein and the induction of a T cytotoxic response against a peptide overlapping the splicing junction zone makes it possible to implement vaccination immunotherapy in addition to standard treatments (anti-CD20 antibody (Rituximab)) of diseases associated with B lymphocyte dysfunction or acute transplant rejection. This vaccination may be performed directly with a peptide, or using a recombinant vectors encoding said peptide.

In this way, the present invention also relates to the use of all or part of a polypeptide according to the invention or all or part of a recombinant vector according to the invention for preparing a drug. According to a preferred embodiment, said polypeptide comprises at least one sequence selected from the group comprising SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13. According to a more preferred embodiment, said polypeptide consists of a polypeptide having a sequence selected from the group comprising SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13.

The present invention also relates to the use of a nucleic acid sequence encoding a polypeptide comprising at least one sequence selected from the group comprising SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 for preparing a drug. According to a preferred embodiment, the use of a nucleic acid sequence encoding a polypeptide having a sequence consists of a sequence selected from the group comprising SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13 for preparing a drug.

According to a more preferred embodiment of said uses for preparing a drug, said polypeptide comprises at least one sequence such as SEQ ID No: 9. According to one particularly preferred embodiment, the use according to the invention is characterised in that said polypeptide consists of a polypeptide having a sequence such as SEQ ID No: 9.

According to a preferred embodiment, said medicinal product is for improving the efficacy of the treatment comprising the use of an anti-CD20 antibody. According to a more preferred embodiment, said anti-CD20 antibody is Rituximab.

According to a preferred embodiment, said drug is for treating or preventing B haemopathies, Follicular Lymphomas (FL), Chronic lymphocytic leukaemia (CLL), B-cell acute lymphoblastic leukaemia (ALL), mantle cell lymphoma (ML), B-cell lymphomas, Myeloma and Waldenström's Disease (WD).

The present invention also relates to a polypeptide having a sequence selected from the group comprising SEQ ID NO: 6, SEQ ID NO: 7, SEQ ID NO: 8, SEQ ID NO: 9, SEQ ID NO: 10, SEQ ID NO: 11, SEQ ID NO: 12 and SEQ ID NO: 13.

A further approach may be a gene transfer, encoding the antibody according to the invention, thus retargeting T lymphocytes against this protein. The development of a monoclonal antibody against this protein will make it possible in parallel to identify the sequences encoding the hypervariable regions (CDR3) of light and heavy Ig chains. The sequences identified can thus be transfected with T cells by gene transfer; coupling with a suicide gene could make it possible to control the anti-ΔCD20 T response although it will be limited to activated tumour T cells expressing this form of protein. In this way, the present invention also relates to the use of an antibody according to the invention or a nucleic acid sequence encoding said antibody or a vector comprising said nucleic acid sequence for preparing a drug, and preferably for preparing a drug for treating diseases from the list associated with B lymphocyte dysfunction as described in this application.

CD20 is both a membrane marker, since it is expressed on the surface of B cells, but also a "susceptibility" gene, since encodes the target molecule of the anti-CD20 antibody treatment (Rituximab) in some haemopathies. These two properties may be used in gene therapy, in order to modify T cells (not normally expressing CD20) ex vivo (e.g. retrovirally) or in vivo. This is particularly useful for modulating and controlling post-bone marrow allograft complications, caused by T lymphocytes (TLs). In this way, after gene modification, the cells can be selected (e.g. by means of an immunomagnetic system) on the basis of expression of CD20 (not normally expressed by TLs) and can be targeted in vivo by anti-CD20 antibodies (Rituximab) in the event of complications (Graft versus Host Disease, GvHD).

While the use of the CD20 gene in gene modification protocols is of interest as a selection marker and as a susceptibility gene, various studies have demonstrated instability of the expression of this gene with a retrovirus LTR promoter with the use thereof as a susceptibility gene. The production of alternative splicing of the CD20 gene may be a source of modulation of the expression. Moreover, we demonstrated the presence of alternative transcripts in retroviral sequence packaging lines transfected with a vector carrying "full length" CD20 cDNA. This line will thus generate ΔCD20 retroviral particles which can infect target cells, but with no surface CD20 expression, which would limit the efficacy of retroviral transduction. Furthermore, the transduced target cells express the spliced form of the CD20 transcripts, which may impair the susceptibility thereof to Rituximab.

In this way, the discovery of alternative splicing, and of donor and acceptor sites for this splicing, makes it possible to produce nucleic acid sequences encoding native CD20 and comprising modifications on said donor and/or acceptor sites to prevent said alternative splicing. In this way, the present invention relates to a nucleic acid sequence encoding CD20 characterised in that it does not comprise an alternative splicing site. According to a preferred embodiment, said sequence comprises a sequence such as SEQ ID NO: 5 and particularly preferably, said sequence consists of a sequence such as SEQ ID NO: 5. The present invention also relates to recombinant vectors as previously defined comprising said nucleic acid sequence. The present invention also relates to viral particles comprising said recombinant vectors, said recombinant vectors associated with one or a plurality of compounds facilitating the introduction thereof into a host cell as defined above and host cells (as defined above) comprising said recombinant vector. The present invention also relates to the use of said nucleic acid sequence or of said recombinant vector for preparing a drug, and preferentially for preparing a drug for improving the efficacy of a treatment comprising the use of an anti-CD20 antibody, and more preferentially said anti-CD20 antibody is Rituximab.

The present invention also relates to pharmaceutical compositions comprising polypeptides, nucleic acid sequences, the antibodies and/or oligonucleotides according to the invention and a pharmaceutically acceptable buffer.

EXPERIMENTS

1. Demonstration of Alternative Splicing of Gene Encoding CD20

In order to close the cDNA encoding CD20 in retroviral plasmid skeleton, we amplified, by RT-PCR, using RNA extracted from the DAUDI B line, the segment corresponding to the entire encoding portion (CDS) of CD20 protein, using 2 primers covering "start" and "stop" codons, respectively.

Electrophoresis of the PCR products revealed 2 distinct bands, one having the expected size of 894 bp and the other having a size less than 393 bp and identical intensity.

Sequencing and alignment of NCBI Genebank revealed a sequence corresponding to the fragment encoding CD20 gene, deleted in the central portion thereof of 501 bp, retaining the "start" and "stop" codons. The analysis of the deletion on the protein demonstrates that the transmembrane portion is practically completely deleted, which does not favour fixation of this protein on the cell membrane surface.

The truncated protein has a sequence of 131 amino acids for a predictive molecular weight of 15 kD and includes the intracytoplasmic C-terminal domain, a small portion of the first transmembrane domain and the end of the intracytoplasmic N-terminal domain. The potential truncated protein is not fixed on the membrane due to lack of expression of the 4 transmembrane segments, as demonstrated by confocal microscopy imaging, by cell line transfection with a vector expressing a wtCD20/GFP or ΔCD20/GFP fusion protein. The wtCD20Δ/GFP or CD20/GFP protein was expressed in 293T eukaryote cells after transfection with the pcDNA3.1 CT topo expression vector (inVitrogen). Since the GFP protein was cloned within the scope of the reading of the CD20 sequence (Δ or WT). The GFP protein was detected by direct excitation (green colour) and the wtCD20 protein by an anti-CD20 antibody coupled with TIRTC (red colour). In this way, the labelling is cytoplasmic in the cells transfected with the truncated form of CD20, whereas essentially membranous co-location of the green and red marks corresponding to GFP and wtCD20 is observed. This confirms that ΔCD20 is limited to the cytoplasm.

The analysis of the wild sequence encoding the CD20 gene (WTCD20) using splicing site, splicing donor site and acceptor site predictive software (NNSPLICE v0.9) demonstrated the presence of a donor site (DS) and a cryptic acceptor site (AS), corresponding exactly to the sequence encoding the deleted CD20 gene (ΔCD20). More in-depth research, with other software suites (Netgene 2) detected a branching site, locating on some twenty base pairs of the acceptor site.

1. Expression of ΔCD20 Protein a. Western Blot Detection

Using B cell lines, we tested by means of Western Blot, with anti-CD20 available antibodies recognising the C-terminal part of the protein (Thermo Fischer, #RB9013), for the presence of a truncated protein (with no transmembrane part, thus cytoplasmic) encoded by the spliced transcripts. In this way, we demonstrated, in addition to the expected band corresponding to the wild CD20 protein, the presence of a band of expected size (~17 KD) corresponding to ΔCD20 protein. This protein is not expressed in T lines.

2. ΔCD20: Diagnostic and/or Prognostic Molecular Biomarker for B Haemopathies or Post-Kidney Allograft Complication (Acute Rejection, Lymphomas)

a. Alternative ΔCD20 Transcripts and B Haemopathies

We screened, with a qualitative PCR test, amplifying the entire encoding sequence (flCD20 PCR), other lines derived from various types of B haemopathies (Burkitt, pre-B ALL, transformed B-EBV) and demonstrated that the short form of the CD20 transcript was present in all B lines and absent in T lines. We then developed a sensitive and specific PCR tool (ΔCD20 PCR), by designing a primer covering the splicing junction site. This novel tool only detects the short form of the mRNA and thus avoids PCR competition phenomena, incompatible with high sensitivity.

Using this more effective PCR tool, we tested for the short form of CD20 on PBMCs or, for more sensitivity, on CD19+ or CD20+ B cells from 5 healthy donors, without detecting same. Specific screening for the truncated transcript, using our sensitive PCR tool displayed a positive signal on the lines and a negative signal on the PBMCs, suggesting the presence of this splicing mechanism in EBV transformed cells, in malignant cells and absence in normal B cells. This truncated form of CD20 RNA is thus the signature of a B cell activation state associated with the malignant phenotype thereof.

b. ΔCD20 Diagnostic Quantification in Various Types of B Haemopathies

To illustrate the possibility of using ΔCD20 transcript quantification in diagnostics for some haemopathies, we applied our QRTPCR assay to various types of B haemopathies. The quantification of both forms (full length and truncated) was carried out against a serial dilution range, of known quantity, of standard plasmids comprising the wt or Δ forms of CD20. Calculating the ratio R=[ΔCD20/(wtCD20+ΔCD20)]×100 makes it possible to express the relative quantity of CD20 transcript in relation to the wild form. We thus demonstrated differential expression of these alternative transcripts in various B haemopathies. We quantified the spliced form of ΔCD20 [expressed as a % of ΔCD20: R=(ΔCD20/wtCD20+ΔCD20)×100] in B-EBV lines transformed in vitro (2.9±4.51%, n=6), in purified CD19+ tonsillectomy cells (9±2.2%, n=7) and B-blasts produced in vitro (14±7.8%, n=5). Advantageously, we quantified ΔCD20 at 3.6±5.1% in B-ALL (n=27), 3.9±5.3% in follicular lymphomas (n=5); 2.9±4.5% in mantle cell lymphomas (n=6); 3.2±2.2% in high grade lymphomas (n=5); and 0.1±0.2% in B-CLL (n=8).

c. ΔCD20: Residual Disease Marker (RDM)

A further possibility would also be that of using our real-time PCR quantification assay to monitor treatment efficacy (chemotherapy optionally associated with Rituximab -Rx-, for example). This test is ideal for haemopathies not having characteristic molecular or phenotypic markers. The ΔCD20 quantification kinetics was compared with the expression of standard molecular markers such as BCR/ABL (p190) transcripts and cyclin D1 for ALL-B and mantle cell lymphoma, respectively. We demonstrated a correlation between the usual markers (cyclin D1 and BCR/Abl p190) and ΔCD20.

3. ΔCD20 Protein, Potential Therapeutic Target a. Resistance to an Anti-CD20 Antibody (Rituximab)

We established Rx resistances in vitro using B lines, by exposing them to different doses and times. In vitro susceptibility tests confirmed resistance acquisition.

Very advantageously, we demonstrated, by means of Western Blot, an intensification of the signal of the truncated form of CD20 protein according to the Rx resistance acquisition of the population. More specifically, we quantified the mRNA encoding ΔCD20 in the cells of patients suffering from follicular lymphoma (n=3) or mantel cell lymphoma (n=3). We observed that Rituximab resistance acquisition was, in each case, correlated with an increase in the quantity of mRNA encoding ΔCD20 (mean×3.38).

b. Construction of ΔCD20-Specific Oligopeptides.

In this way, using the translation of the ΔCD20 mRNA sequence, we used the SYFPEITHI base to design peptides overlapping (AA30 to AA39) the alternative splicing junction zone and thus specific for the ΔCD20 form). Using a predictive proteasome cleavage tool (PAProC), 2 potentially immunogenic peptides of interest (No. 4-RMS and No. 7-SLE), since they are potentially prepared with proteoasome enzymes and restricted for HLA-A*0201, were detected.

The peptides corresponding to these sequences were synthesised by MILLEGEN (LABEGE, France) and dissolved in 20% DMSO and stored at −80° C.

The bonding affinity of the peptides identified for the MHC molecule in question and the stability of the peptide/MHC I molecule complex were confirmed in vitro (data not shown).

c. T Cytotoxic Response Induction by Peptide Vaccination

The immunogenicity of the ΔCD20a peptides was evaluated by generating CTL on HLA-A2/DR1 and Knock-Out (KO) transgenic mice for H-2 class I and II.

The mice (4 per group) are immunised with pools of 2 or 3 peptides (2 injections at the base of the tail at an 8-day interval) with: 50 µg of each peptide, 100 µg of helper peptide (20 mers peptide from CMV-specific pp65), the whole co-emulsified with incomplete Freud adjuvant.

Seven days after the second immunisation, the spleens of the mice are removed and the splenocytes are re-stimulated in vitro with 4 µg/ml of each peptide separately. On the fifth day of culture, the respondent populations are tested to determine specific cytotoxicity. The cells, with conclusive cytotoxicity, are re-stimulated in vitro at one-week intervals to obtain specific CTLs.

RMAS-HHD cells are used as targets to study cytotoxicity. These target cells are filled with 10 µg/ml of the peptide under test, or a non-relevant control peptide, at 37° C. for 90 minutes and labelled with 100 µCi of 51Cr for 90 minutes, and washed three times. The splenocytes are distributed in V-bottomed 96-well plates (3×10$^3$ cells/well in 100 µl of RPMI 1640+ 10% foetal calf serum). Then, 100 µl of the effector cells (effector cell/target cell ratio=30:1; 10:1; 3:1 and 1:1) are added to the wells and the plates are incubated at 37° C. for 4 hours. After incubation, 50 µl of supernatant is collected, transferred into specific plates (Lumaplate) and the radioactivity is measured in a γ counter. The specific lysis percentage is calculated using the formula:

$$[(\text{experimental 51 Cr release} - \text{spontaneous 51 Cr release}) / (\text{maximum 51 Cr release} - \text{spontaneous 51 Cr release})] \times 100.$$

Three out of 4 mice from immunisation group A clearly developed T cytotoxic response against peptide No. 4 and no response against a third-party peptide BMLF1, specific for EBV, thus indicating the specificity of the response.

These results demonstrate that immunisation with the RMS peptide generates CTLs killing RMAS-HHD targets charged with said peptide, but not cells charged with the non-relevant peptide.

These studies clearly demonstrate that we were able to obtain an anti-ΔCD20 CTL response which could be used to improve the anti-CD20 antibody treatment and prevent or eliminate the persistence of CD20+ tumour B lymphocytes (expressing ΔCD20 protein).

4. Targeted Mutagenesis Production of a Sequence Encoding CD20 not Suitable for Alternative Splicing.

We thus undertook to mutate the wild sequence of the human CD20 gene, to limit the formation of these alternative transcripts. The mutation of the acceptor site to modify the nucleotide sequence and preserve the reading frame and thus the amino acid sequence maintaining the AA Gln, encoded by the CAG or CAA codon. The mutation was carried out on nucleotide 612 (coordinate based on the first base of the ATG—start codon): −nt612G>A. After targeted mutagenesis, we verified, by sequencing, the mutation of a single base pair on the acceptor site. Finally, we demonstrated that the mutated CD20 gene sequence (mutCD20) did not generate further alternative transcripts. A flow cytometry analysis of the CD20 expression proves that the expression is maintained and that the protein is indeed expressed on the membrane.

The invention claimed is:

1. A diagnostic kit comprising at least one specific oligonucleotide probe for the mRNA encoding a polypeptide having an amino acid sequence substantially identical to that of SEQ ID NO: 2, wherein the diagnostic kit comprises at least one oligonucleotide comprising a sequence identical to any one of SEQ ID NO: 14, SEQ ID NO: 15, and SEQ ID NO: 17 or wherein the diagnostic kit comprises at least one oligonucleotide consisting of a sequence identical to SEQ ID NO: 16.

2. The diagnostic kit according to claim 1 wherein the diagnostic kit comprises at least one oligonucleotide consisting of a sequence identical to any one of SEQ ID NO: 14, SEQ ID NO: 15, and SEQ ID NO: 17.

* * * * *

SEQUENCE LISTING

```
<160> NUMBER OF SEQ ID NOS: 17

<210> SEQ ID NO 1
<211> LENGTH: 393
<212> TYPE: DNA
<213> ORGANISM: Homo sapiens

<400> SEQUENCE: 1
atgacaacac ccagaaattc agtaaatggg actttcccgg cagagccaat gaaaggccct      60
attgctatgc aatctggtcc aaaaccactc ttcaggagga tgtcttcact ggaacttgta     120
atagctggca tcgttgagaa tgaatggaaa agaacgtgct ccagacccaa atctaacata     180
gttctcctgt cagcagaaga aaaaaagaa cagactattg aaataaaaga agaagtggtt     240
gggctaactg aaacatcttc ccaaccaaag aatgaagaag acattgaaat tattccaatc     300
caagaagagg aagaagaaga aacagagacg aactttccag aacctcccca agatcaggaa     360
tcctcaccaa tagaaaatga cagctctcct taa                                  393

<210> SEQ ID NO 2
<211> LENGTH: 130
<212> TYPE: PRT
<213> ORGANISM: Homo sapiens

<400> SEQUENCE: 2

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Glu Leu Val Ile Ala Gly Ile Val Glu Asn Glu
        35                  40                  45

Trp Lys Arg Thr Cys Ser Arg Pro Lys Ser Asn Ile Val Leu Leu Ser
    50                  55                  60

Ala Glu Glu Lys Lys Glu Gln Thr Ile Glu Ile Lys Glu Glu Val Val
65                  70                  75                  80

Gly Leu Thr Glu Thr Ser Ser Gln Pro Lys Asn Glu Glu Asp Ile Glu
                85                  90                  95

Ile Ile Pro Ile Gln Glu Glu Glu Glu Glu Thr Glu Thr Asn Phe
            100                 105                 110

Pro Glu Pro Pro Gln Asp Gln Glu Ser Ser Pro Ile Glu Asn Asp Ser
        115                 120                 125

Ser Pro
    130

<210> SEQ ID NO 3
<211> LENGTH: 1915
```

```
<212> TYPE: DNA
<213> ORGANISM: Homo sapiens

<400> SEQUENCE: 3
agcgatttca tcttcaggcc tggactacac cactcaccct cccagtgtgc ttgagaaaca    60
aactgcaccc actgaactcc gcagctagca tccaaatcag cccttgagat ttgaggcctt   120
ggagactcag atcctgaaca agagagaaca aaatctctac tttgatggaa cttccattct   180
gtggggaaga gactgacaat aagcaattaa ataaataaga actcagcagt aggccttgcc   240
tcagatccaa ggtcactcgg aagaggccat gtctaccctc aatgacactc atggaggaaa   300
tgctgagaga agcattcaga tgcatgacac aaggtaagac tgccaaaaat cttgttcttg   360
ctctcctcat tttgttattt gttttatttt taggagtttt gagagcaaaa tgacaacacc   420
cagaaattca gtaaatggga ctttcccggc agagccaatg aaaggcccta ttgctatgca   480
atctggtcca aaaccactct tcaggaggat gtcttcactg gtgggcccca cgcaaagctt   540
cttcatgagg gaatctaaga cttgggggc tgtccagatt atgaatgggc tcttccacat    600
tgccctgggg ggtcttctga tgatcccagc agggatctat gcacccatct gtgtgactgt   660
gtggtaccct ctctggggag gcattatgta tattatttcc ggatcactcc tggcagcaac   720
ggagaaaaac tccaggaagt gtttggtcaa ggaaaaatg ataatgaatt cattgagcct    780
ctttgctgcc atttctggaa tgattctttc aatcatggac atacttaata ttaaaatttc   840
ccatttttta aaatggaga gtctgaattt tattagagct cacacaccat atattaacat    900
atacaactgt gaaccagcta atccctctga gaaaaactcc ccatctaccc aatactgtta   960
cagcatacaa tctctgttct tgggcatttt gtcagtgatg ctgatctttg ccttcttcca  1020
ggaacttgta atagctggca tcgttgagaa tgaatgaaa agaacgtgct ccagacccaa   1080
atctaacata gttctcctgt cagcagaaga aaaaaagaa cagactattg aaataaaga    1140
agaagtggtt gggctaactg aaacatcttc ccaaccaaag aatgaagaag acattgaaat  1200
tattccaatc caagaagagg aagaagaaga aacagagacg aactttccag aacctcccca  1260
agatcaggaa tcctcaccaa tagaaaatga cagctctcct taagtgattt cttctgtttt  1320
ctgtttcctt ttttaaacat tagtgttcat agcttccaag agacatgctg actttcattt  1380
cttgaggtac tctgcacata cgcaccacat ctctatctgg cctttgcatg gagtgaccat  1440
agctccttct ctcttacatt gaatgtagag aatgtagcca ttgtagcagc ttgtgttgtc  1500
acgcttcttc ttttgagcaa ctttcttaca ctgaagaaag gcagaatgag tgcttcagaa  1560
tgtgatttcc tactaacctg ttccttggat aggcttttta gtatagtatt ttttttttgtc  1620
attttctcca tcaacaacca gggagactgc acctgatgga aagatatat gactgcttca   1680
tgacattcct aaactatctt ttttttattc cacatctacg ttttttggtgg agtcccttt   1740
gcatcattgt tttaaggatg ataaaaaaaa ataacaacta gggacaatac agaacccatt  1800
ccatttatct ttctacaggg ctgacattgt ggcacattct tagagttacc acaccccatg  1860
agggaagctc taaatagcca acacccatct gttttttgta aaaacagcat agctt        1915

<210> SEQ ID NO 4
<211> LENGTH: 297
<212> TYPE: PRT
<213> ORGANISM: Homo sapiens

<400> SEQUENCE: 4

Met Thr Thr Pro Arg Asn Ser Val Asn Gly Thr Phe Pro Ala Glu Pro
1               5                   10                  15
```

```
Met Lys Gly Pro Ile Ala Met Gln Ser Gly Pro Lys Pro Leu Phe Arg
         20                  25                  30

Arg Met Ser Ser Leu Val Gly Pro Thr Gln Ser Phe Phe Met Arg Glu
             35                  40                  45

Ser Lys Thr Leu Gly Ala Val Gln Ile Met Asn Gly Leu Phe His Ile
     50                  55                  60

Ala Leu Gly Gly Leu Leu Met Ile Pro Ala Gly Ile Tyr Ala Pro Ile
 65                  70                  75                  80

Cys Val Thr Val Trp Tyr Pro Leu Trp Gly Gly Ile Met Tyr Ile Ile
                 85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 5
<211> LENGTH: 893
<212> TYPE: DNA
<213> ORGANISM: Artificial Sequence
<220> FEATURE:
<223> OTHER INFORMATION: Mutated gene, encoding CD20, lacking the splice
      acceptor site responsible for alternative splicing.

<400> SEQUENCE: 5
atgacaacac ccagaaattc agtaaatggg actttcccgg cagagccaat gaaaggccct      60
attgctatgc aatctggtcc aaaaccactc ttcaggagga tgtcttcact ggtgggcccc     120
acgcaaagct tcttcatgag ggaatctaag actttggggg ctgtccagat tatgaatggg     180
ctcttccaca ttgccctggg gggtcttctg atgatcccag cagggatcta tgcacccatc     240
tgtgtgactg tgtggtaccc tctctgggga ggcattatgt atattatttc cggatcactc     300
ctggcagcaa cggagaaaaa ctccaggaag tgtttggtca aggaaaaaat gataatgaat     360
tcattgagcc tctttgctgc catttctgga atgattcttt caatcatgga catacttaat     420
```

```
attaaaattt cccattttt aaaaatggag agtctgaatt ttattagagc tcacacacca    480
tatattaaca tatacaactg tgaaccagct aatccctctg agaaaaactc cccatctacc    540
caatactgtt acagcataca atctctgttc ttgggcattt tgtcagtgat gctgatcttt    600
gccttcttcc aagaacttgt aatagctggc atcgttgaga atgaatgaa aagaacgtgc    660 tccagaccca atctaacat agttctcctg tcagcagaag aaaaaaaaga acagactatt    720
gaaataaaag aagaagtggt tgggctaact gaaacatctt cccaaccaaa gaatgaagaa    780
gacattgaaa ttatccaatc caagaagagg aagaagaaga aacagagacg aactttccag    840
aacctcccca agatcaggaa tcctcaccaa tagaaaatga cagctctcct taa    893
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Leu Phe Arg Arg Met Ser Ser Leu Glu
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Phe Arg Arg Met Ser Ser Leu Glu Leu
1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Arg Arg Met Ser Ser Leu Glu Leu Val
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Arg Met Ser Ser Leu Glu Leu Val Ile
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10
```

```
Met Ser Ser Leu Glu Leu Val Ile Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Ser Ser Leu Glu Leu Val Ile Ala Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Ser Leu Glu Leu Val Ile Ala Gly Ile
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Leu Glu Leu Val Ile Ala Gly Ile Val
1               5

<210> SEQ ID NO 14
<211> LENGTH: 18
<212> TYPE: DNA
<213> ORGANISM: Artificial Sequence
<220> FEATURE:
<223> OTHER INFORMATION: Oligonucleotide

<400> SEQUENCE: 14
gatgtcttca ctggaact                                                  18

<210> SEQ ID NO 15
<211> LENGTH: 21
<212> TYPE: DNA
<213> ORGANISM: Artificial Sequence
<220> FEATURE:
<223> OTHER INFORMATION: oligonucleotide

<400> SEQUENCE: 15
ttaaggagac tgtcattttc t                                              21

<210> SEQ ID NO 16
<211> LENGTH: 21
<212> TYPE: DNA
<213> ORGANISM: Artificial Sequence
<220> FEATURE:
<223> OTHER INFORMATION: oligonucleotide

<400> SEQUENCE: 16
gagccaatga aaggccctat t                                              21
```

```
<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
agctattaca agttccagtg                                                    20
```